US 8,448,496 B2

(12) United States Patent
Huang et al.

(10) Patent No.: US 8,448,496 B2
(45) Date of Patent: May 28, 2013

(54) PIEZOELECTRIC COAGULATION SENSORS

(75) Inventors: Michael Huang, San Jose, CA (US);
Mengya Wu, Santa Clara, CA (US);
Mengyou Wu, Santa Clara, CA (US)

(73) Assignee: Micropoint Bioscience Inc., Santa Clara, CA (US)

( * ) Notice: Subject to any disclaimer, the term of this patent is extended or adjusted under 35 U.S.C. 154(b) by 331 days.

(21) Appl. No.: 12/924,281

(22) Filed: Sep. 22, 2010

(65) Prior Publication Data

US 2011/0203367 A1    Aug. 25, 2011

Related U.S. Application Data

(60) Provisional application No. 61/279,542, filed on Oct. 21, 2009.

(51) Int. Cl.
*G01N 9/00* (2006.01)
*G01N 11/10* (2006.01)

(52) U.S. Cl.
USPC .......................................... 73/32 A; 73/54.24

(58) Field of Classification Search
USPC ............. 73/32 A, 54.01, 54.23, 54.25, 54.26, 73/54.27, 54.41
See application file for complete search history.

(56) References Cited

U.S. PATENT DOCUMENTS

| 4,114,423 | A |   | 9/1978  | Wenger |
| 4,920,787 | A | * | 5/1990  | Dual et al. ................... 73/54.41 |
| 4,961,345 | A | * | 10/1990 | Tsuruoka et al. ............. 73/32 A |
| 5,349,844 | A |   | 9/1994  | Lilienfeld |
| 5,383,349 | A | * | 1/1995  | Blake-Coleman ............. 73/32 A |
| 5,892,144 | A | * | 4/1999  | Meller et al. ................ 73/64.42 |
| 6,200,532 | B1|   | 3/2001  | Wu et al. |

FOREIGN PATENT DOCUMENTS

| JP | 05-264301 A | 10/1993 |
| JP | 05-037999 A | 2/1994 |
| JP | 63-144233 A | 6/1998 |

OTHER PUBLICATIONS

International Search Report and Written Opinion for PCT/US2010/002605.

* cited by examiner

*Primary Examiner* — Hezron E. Williams
*Assistant Examiner* — Nathaniel Kolb
(74) *Attorney, Agent, or Firm* — Gary Baker; Quine IP Law Group, P.C

(57) ABSTRACT

This invention provides methods and devices to measure physical characteristics of sample fluids. Samples are introduced into a sample chamber in contact with a mechanically oscillating working member. The vibrations are received by a piezoelectric sensor transducer and correlated to a sample characteristic, such as viscosity or density. The devices include a sample chamber in contact with one or more working members actuated by a piezoelectric actuator and/or monitored by a piezoelectric sensor.

48 Claims, 5 Drawing Sheets

PIEZOELECTRIC COAGULATION SENSORS

CROSS-REFERENCE TO RELATED APPLICATIONS

This application claims priority to and benefit of a prior U.S. Provisional Application No. 61/279,542, Piezoelectric Coagulation Sensors, by Michael Huang, et al., filed Oct. 21, 2009. The full disclosure of the prior application is incorporated herein by reference.

FIELD OF THE INVENTION

The present inventions are directed to piezoelectric detectors and methods of detecting, e.g., physical properties of a fluid using piezoelectric devices. An energized piezoelectric transducer can contact a sample to determine, e.g., the mass, density or viscosity of the sample through correlation with a resultant vibrational frequency. A sample can be brought into contact with a piezoelectric transducer providing a physical waveform. The waveform can be detected and correlated with a physical characteristic of the sample.

BACKGROUND OF THE INVENTION

Piezoelectric devices are used in various detector systems, e.g., to detect the presence of specifically adsorbed materials on a surface or to detect the coagulation state of a protein solution. However, many of these designs are difficult or expensive to manufacture, or are not compatible with at a micro-scale designs for testing of very small samples.

Various techniques have been used over the years to determine the coagulation status of blood. The standard for coagulation determinations in medical technology for some time was the fibrometer, which detects coagulation directly with a mechanical probe. Recently, devices have been introduced that detect changes in the coagulation status of blood or plasma indirectly by measuring changes in optical or electrical characteristics of the fluid with time. However, there is a need for a microscale device that directly measures physical parameters, e.g., of clotting blood.

A fibrometer is a device with a heat block to condition the temperature of a sample to be tested, a timer, and a mechanical probe that moves in the sample to detect when a clot has formed. A couple of drops of citrate anti-coagulated plasma is held in the heat block with the probe positioned above. At the instant a technician injects a coagulant into the plasma he presses a button that starts a timer and drops the moving probe down into the plasma. The timer stops at the time when the plasma becomes coagulated enough to stop the probe from moving. Of course, one can see that precision of this assay can vary significantly depending on the skill of the technician. In addition the required sample size can be excessive, especially considering the required redundant and confirmatory retesting.

A macro-scale device and method for performing blood coagulation assays is described in Wu, et al. (U.S. Pat. No. 6,200,532). Devices for performing prothrombin times and activated partial thromboplastin times and other clotting parameters are disclosed. The devices include, e.g., a disposable cartridge containing a sample inlet for sample delivery, a capillary channel to provide fluid flow, a reaction chamber with an appropriate dry reagent for a specific assay, a magnetic bender, and a piezoelectric sensor. The magnetic bender is driven by an electromagnetic field generator and is attached onto a piezoelectric film sensor in contact with a blood sample. Electric signals (voltages) generated at the piezo film are detected by a detector circuit and characterized by frequency and amplitude. The voltages from the piezo film can be correlated to a biochemical reaction in the reaction chamber. For example, blood coagulation can be detected as reduced amplitude signals from the piezo sensor as the solidifying clot reduces freedom of piezo film movement. However, such a device is hard to manufacture and operate at a micro-scale.

In Meller (U.S. Pat. No. 5,892,144), a biosensor is provided for measuring changes in viscosity, density and/or mass in a fluid. The piezoelectric element is a disk of piezoelectric film in a chamber. According to the invention, the reagents necessary for the test are contained in a support matrix in contact with a measurement surface of a piezoelectric element. An oscillator vibrates the piezo disk and density of a sample in contact with the disk can be determined by an evaluation circuit. Such a device requires direct contact of the sample with the piezo film and its associated electrodes, or provision of additional insulator layers that can interfere with the sensitivity of the device. The mass of the sensor (typically, a quartz crystal) relative to the sample can also reduce the sensitivity of the device.

In view of the above, a need exists for a microscale device that automates coagulation assay steps. It would be desirable to measure a sample viscosity without direct contact of sample with electrically energized system components. It would be beneficial to have micro-scale and signal enhancing designs to reduce sample size and enhance assay sensitivity. The present invention provides these and other features that will be apparent upon review of the following.

SUMMARY OF THE INVENTION

Methods and devices of the invention employ piezoelectric actuators and sensors in combination with associated working members to determine a physical property (such as viscosity or density) of a sample in a sample chamber. The devices can be, e.g., an assay cartridge with an actuator working member energized by a piezoelectric device in electric contact with an oscillator, and a sensor working member transmitting vibrations from the sample to a piezoelectric sensor transducer in electric contact with a detector. Methods include, e.g., introducing a sample of interest into a sample chamber, vibrating the sample with a piezoelectric actuator through a working member, receiving transmitted vibrations with a sensor and correlating the vibrations to a physical property of the sample. In many embodiments, the device is a microelectricalmechanical (MEMS) device.

In one embodiment of the devices, a sensor comprises a membrane sample contact surface (sensor working member) functionally mounted to an annular piezoelectric sensor. For example, a device for measuring physical characteristics of a sample can include an annular piezoelectric transducer comprising a central opening, a working member membrane comprising a sample contact surface and mounted across a central axis of the transducer central opening, and a detector circuit in electrical contact with the transducer so that vibrations in the working member membrane are transmitted to the transducer inducing changes in electrical parameters (such as, e.g., a waveform, electrical resistance, voltage, resonance frequency or current) of the transducer detectable by the detector.

In the annular/membrane embodiment, there are several preferred configurations. The device can have an annular transducer with a central aperture with a dome shaped working member membrane mounted across the aperture. In a preferred embodiment, the membrane is dome shaped, projecting away from the central opening. The membrane can be mounted across the aperture of an annular mounting ring, e.g., with the ring between the membrane and the annular transducer. The sensor can be configured with the central opening having a circular circumference, the central opening having a diameter ranging from about 10 mm to about 0.1 mm or about 2 mm to about 0.5 mm, and/or with the membrane having a thickness ranging from about 0.2 mm to about 0.05 mm.

In another aspect of the inventive devices, the sensor has an actuator working member that also functions as sensor working member. For example, the device can include a piezoelectric transducer, an oscillator in electrical contact with the transducer, a working member in functional contact with the actuator and comprising a sample contact surface, and a detector in electrical contact with the transducer so that vibrations can be imparted to the working member from the transducer and electronic parameters can be detected in the same transducer by the detector.

In still another configuration, the device includes separate actuator and sensor transducers. For example, a device for detecting physical characteristics of a sample can include a detection chamber defining an inner space, a piezoelectric actuator in functional contact with a working surface in contact with the inner space, and a piezoelectric sensor in functional contact with at sensor surface in contact with the inner space. The vibrations from the actuator are transmitted to the working surface, through the chamber space, and to the sensor surface to be detected by the sensor. In a typical embodiment, the inner space has at least one microscale dimension, e.g., less than 0.2 mm. In preferred embodiments, the actuator is in functional contact with the working surface through a working member. In some embodiments, separate actuators and sensors are in direct contact with each other; but in preferred embodiments, the sensor and actuator are typically not in direct contact, e.g., not laminated together. In many embodiments of systems with separate actuator and sensor, the actuator comprises a major surface (e.g., sample contact surface) in a plane (e.g., largest substantially planar dimension) that is not parallel to the major surface plane of the sensor.

In many of the devices, an electrical oscillator is in electrical contact with the transducer (actuator) so that electrical oscillations from the oscillator induce vibrations in the transducer, and associated working member. Actuators can be configured to provide a working mode appropriate to enhance interaction of the working member with the sample, e.g., with the transducer configured in shear-mode or in transverse mode.

Samples for analysis can be any sample of interest and suitable to a particular device. For example, typical samples can be any fluid or gelatinous material of interest to investigators. Exemplary samples include whole blood, blood plasma, clotted blood, cerebrospinal fluid (CSF), synovial fluid, amniotic fluid, glass, sugar, food recipe compositions, plastics resins, and/or the like.

The sample chambers of the devices can define an inner space and inner surface. The sample contact surfaces of working members can be in fluid contact and within the sample chamber space. A reagent can be in contact with or within the inner space. It is an aspect of the invention that the sample is in contact with a working member sample contact surface. In one aspect, at least part of sample contact surface is not between the sample and the transducer. In some embodiments the sample chamber is other than a channel leading to or from the chamber.

Working members can provide leverage and working surface area advantages, while isolating the sample from contact with the transducers. The working members can be any suitable shape, e.g., for a particular combination of sample, transducer and sample chamber. In an embodiment, the working member is in functional contact with the transducer at a mounting surface, and most of the sample contact surface is not in a plane parallel to the mounting surface (e.g., the working member is a beam cantilevered into the sample chamber or has a dome shape). In some embodiments, the working member is a cantilevered beam in contact with the transducer at one end but not at the opposite end.

Detectors can receive a signal, such as a voltage, resistance, current or waveform, from a sensor transducer, e.g., to detect a change in viscosity, mass or density of a fluid in contact with the sample contact surface according to a correlation with the electrical parameter. For example, in many cases, the detected frequency and voltage amplitude are inversely related to the viscosity or mass of the sample in contact with the sensor contact surface.

The present inventions include methods of determining a physical characteristic of a sample. For example, methods can include detecting coagulation with the membrane sensor. Such methods can comprise providing a piezoelectric transducer with a central opening, providing a working member membrane having a sample contact surface and mounted across the central opening of the transducer, contacting the sample contact surface with a sample, vibrating the working member membrane with the transducer, detecting a voltage, resistance or current in the transducer, and correlating the detected voltage, resistance or current with the physical characteristic of the sample. Detecting can include measuring the voltage, resistance or current at two or more time points, thereby detecting a change in the viscosity of the sample over time. The method can further comprise providing a sample chamber defining an inner space in fluid contact with the sample contact surface and retains the sample, and providing a reagent in the space that reacts with the sample to provide a change in sample viscosity.

In another method of detecting a sample physical characteristic, a piezoelectric transducer is provided in functional contact with a working member having a sample contact surface, a sample is provided in contact with the contact surface, a vibration is induced from the piezoelectric transducer through the working member contact surface into the sample, a detector is provided in electrical contact with the transducer, an electrical parameter of the transducer is detected with the detector, and the parameter is correlated with the physical characteristic of the sample in contact with the sample contact surface.

In another method, physical characteristics of a sample are detected with separate piezoelectric actuators and sensors. For example, such a method of detecting a physical characteristic of a sample can include providing a sample chamber defining an inner space, providing a piezoelectric actuator in functional contact with a working surface in contact with the inner space, providing a piezoelectric sensor in functional contact with at sensor surface in contact with the inner space, introducing a sample into the chamber inner space, vibrating the piezoelectric actuator to transmit vibrations from the actuator working surface through the sample to the sensor surface, detecting the transmitted vibrations at the sensor, and correlating the detected vibrations to the physical characteristic of the sample. Detecting can include measuring the characteristic at two or more time points, thereby detecting a change in the physical characteristic of the sample over time.

The sample can be any of interest for determination of the physical parameter. For example, the sample can be a biological fluid or synthetic polymer, e.g., polymer monomers or blood products. A reagent can be provided in the inner space to reacts with the sample to provide a product that changes the sample characteristic (e.g., viscosity, density, or mass). Where the sample is whole blood or plasma, a clotting time can be determined by detecting a viscosity change.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "samples" can include mixtures of samples, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

A piezoelectric transducer, as used herein, is a piezoelectric device that transduces a physical force input to an electrical output or transduces an electrical input to a physical output. A transducer is a device that converts one type of energy or physical attribute to another for various purposes. There are two general types of transducers: 1) sensors that detect a parameter in one form and report it in another form of energy, e.g., detecting a pressure and reporting a voltage; and 2) actuators that transform electrical energy into mechanical energy. Piezoelectric devices are excellent transducers for MEMS applications. Piezoelectric transducers can generate an electric field or electric potential in response to applied mechanical stress, or can provide a mechanical movement in response to an electric field or electric potential. In the present inventions a single transducer can often function as both a sensor and an actuator, e.g., at once or consecutively. It is understood that in many embodiments of the devices and methods the transducer can be other that a piezoelectric transducer, e.g., an electromagnetic transducer.

A "central axis" of an annular or ring shaped component is a line running through the center of the ring circumference perpendicular to the major plane (circumference) of the ring.

A "working member", as used herein, is a mechanical device that transmits mechanical forces between a sample and a transducer. The working members can provide a mechanical advantage and can act to isolate the sample from direct contact with the transducer. Work is force through a distance. A working surface is a surface in contact with a sample to move the sample with force through a distance, e.g., imparting vibrations. Sensor working surfaces are worked on by the sample, e.g., the sample receiving force through a distance from the sample. Working surfaces are typically the outer surface of a working member in contact with a sample chamber interior space or with a sample in the chamber.

Electrical parameters are measurable electrical phenomenon such as, e.g., an electrical waveform, electrical resistance, voltage, resonance frequency or current. Electrical parameters are typically detectable using an electronic meter, such as, e.g., a voltmeter, ohmmeter, ammeter, oscilloscope, and/or the like. A resonant frequency can be the result of the overall interaction of, e.g., resistance load of the sample and working member influencing the oscillator circuit. Electrical parameters can be measured directly or indirectly. For example, Ohm's law states that the current through a conductor between two points is directly proportional to the potential difference or voltage across the two points, and inversely proportional to the resistance between them. Therefore, given any two parameters, the third can be calculated. Electrical parameters, in the present invention, are typically the electrical output of piezoelectric sensors in response to mechanical stresses (e.g., forces, vibrations, energy, work) received directly from a sample or through a working member.

Vibrations, as used herein, are mechanical oscillations about an equilibrium point. The oscillations may be periodic, such as the motion of a pendulum, or random. In some embodiments a "vibration" can include a single pulse. However, vibrations most typically used in the present inventions have sinusoidal waveforms or square waveforms of a particular wavelength.

Electronic waveforms in the present inventions are electronic oscillations, e.g., measurable as voltage or current waveforms. In many instances, the electronic waveforms can be transduced copies of mechanical waveforms (vibrations) received by a sensor of the invention.

One component is "immediately adjacent" to another component, e.g., if the components are in direct physical contact with each other (e.g., at touching surfaces), or if they are separated from closest contact by a membrane or thin layer.

A "major surface" or plane of a component is a continuous surface that does not include a surface running across the thickness of the component. For example, a major surface of a membrane in a broad planar surface, and not a surface across the thickness, e.g., at the perimeter edge of the membrane. In a three dimensional solid, a surface defined by the two major dimensions (e.g., length and width) can define a major surface, while a surface defined by the least dimension (e.g., thickness or depth) would not be considered a major surface.

Microscale dimensions are dimensions 1000 μm or less, from about 500 μm to about 0.1 μm, from about 100 μm to about 1 μm, or about 10 μm. A MEMS device is microelectromechanical system, having microscale components, such as, e.g., microscale channels, chambers, and working members.

"Viscosity" is a measure of the resistance of a fluid (including gels and semisolids) to deformation by either shear stress or extensional stress, as is known in the art.

BRIEF DESCRIPTION OF THE DRAWINGS

FIG. 4A shows a top down view of an analytical cartridge with a dome actuator/sensor energized by an oscillator, with detection by a detector and comparator. FIG. 4B shows a cross-sectional side view of the dome-shaped working/sensor member in functional contact with an annular piezoelectric actuator/sensor.

DETAILED DESCRIPTION

Devices of the invention for detection of physical characteristics of samples in the invention generally include, e.g., a transducer vibrating a working member in contact with a sample to impart the vibration into the sample. A sensor in contact with the sample picks up the vibrations and sends a signal to a detector circuit, e.g., for correlation of the electrical signal to one or more physical characteristics of the sample. The methods typically include, e.g., introduction of a fluid sample into a sample chamber in contact with a working member and vibrating the member with a piezoelectric transducer, thereby inducing vibrations into the sample, detecting the sample vibrations with a piezoelectric sensor, sending a signal from the sensor to a detector, and correlating the signal to a characteristic of the sample.

Figure 1:
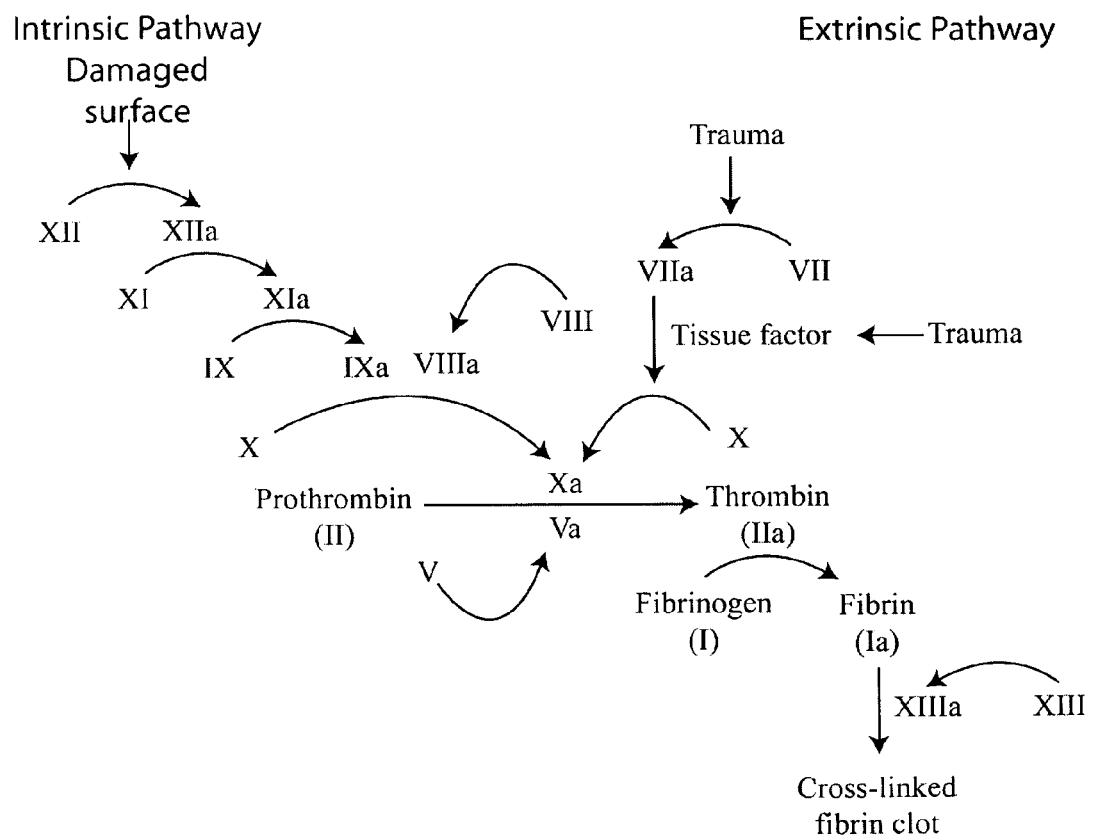
FIG. 1 is a flow diagram showing the intrinsic and extrinsic pathways lead to coagulation of blood plasma.

Many of the devices and methods of the invention can be used to evaluate coagulation in a blood sample. Blood coagulates according to a well-established coagulation cascade of blood protein changes that lead ultimately to coagulation of the blood by conversion of fibrinogen to fibrin. Coagulation can be initiated along the intrinsic contact activation pathway or along the extrinsic tissue factor pathway, as shown in FIG. 1. The two initiation pathways converge at the common pathway wherein prothrombin is converted to thrombin. Thrombin is a serine protease that acts on soluble fibrinogen in plasma to convert it into elongate insoluble fibrin monomers that form a contracting gel (clot).

The intrinsic pathway is typically initiated by formation of the primary complex of high-molecular-weight kininogen (HMWK), prekallikrein, and factor XII on blood contact with exposed collagen. Prekallikrein is converted to kallikrein and factor XII becomes factor XIIa. Factor XIIa converts factor XI into factor XIa. Factor XIa activates factor IX, which forms a tenase complex with cofactor VIIIa, which in turn activates factor X to factor Xa. Activated factor Xa can initiate the final coagulation phase by converting prothrombin into thrombin, which coagulates fibrinogen. This pathway can be evaluated using the activated partial thromboplastin time (aPTT) assay.

The extrinsic tissue factor clotting pathway generates a "thrombin burst", to quickly stop blood flow in response to trauma. Following damage to a blood vessel, factor VII comes into contact with tissue factor (TF), which is present extravascularly in cells, such as stromal fibroblasts and leukocytes, to form an activated complex (TF-VIIa). In the brief following cascade, TF-VIIa activate factor X to factor Xa, which can convert prothrombin to thrombin. This pathway can be evaluated using the prothrombin time (PT) assay.

In the final common pathway, thrombin has a variety of functions. However, its primary role is the conversion of fibrinogen to fibrin, the building block of a hemostatic plug along with platelets. In addition, thrombin activates factors VIII and V and their inhibitor protein C (in the presence of thrombomodulin), and it activates Factor XIII, which forms covalent bonds that crosslink the fibrin polymers that form from activated monomers.

The function of the intrinsic pathway in a plasma sample can be determined using the activated partial thromboplastin time (aPTT) assay. Apart from detecting abnormalities in blood clotting, it is also used to monitor the treatment effects with heparin, a major anticoagulant. A phlebotomist collects blood samples in vacu-tubes with oxalate or citrate to arrest coagulation by binding calcium. The blood sample is then centrifuged to provide blood plasma. To activate the intrinsic pathway in an aPTT assay, phospholipid, an activator (such as silica, celite, kaolin, ellagic acid), and calcium (to reverse the anticoagulant effect of the oxalate) are mixed into the plasma sample. The activated partial thromboplastin time is essentially the time it then takes for a clot to form.

The aPTT can be used in conjunction with the prothrombin time (PT), which measures the function of the extrinsic pathway. In the PT assay, an excess of calcium is added (thereby reversing the anticoagulation effects of citrate) along with tissue factor (also known as factor III or thromboplastin). The PT result is essentially the time it takes tissue factor to coagulate a plasma sample at 37° C.

The present methods and devices can be used to evaluate the density or viscosity of any number of fluid or gel samples. However, we note that the methods and devices are particularly well suited to the performance of blood coagulation assays, such as aPTTs and PTs. For example, the devices can be automated for enhanced assay reproducibility, the devices can directly measure the functional structures of the clot, so the results correlate well with clotting function. The devices can use very small samples to allow multiple assays from very small sample collections.

Devices For Detection of Physical Characteristics in a Fluid Sample

The devices generally include a piezoelectric transducer attached to a working member (such as a cantilever beam or membrane) in fluid contact with a sample chamber. A vibration sensor is typically also in contact with the sample chamber, to receive vibrations transmitted through a sample present in the chamber. A logic circuit (e.g., including a comparator or regression analysis software) can receive signals from the sensor and correlate them to a physical characteristic of the sample, such as a viscosity or polymerization state.

Figure 2:
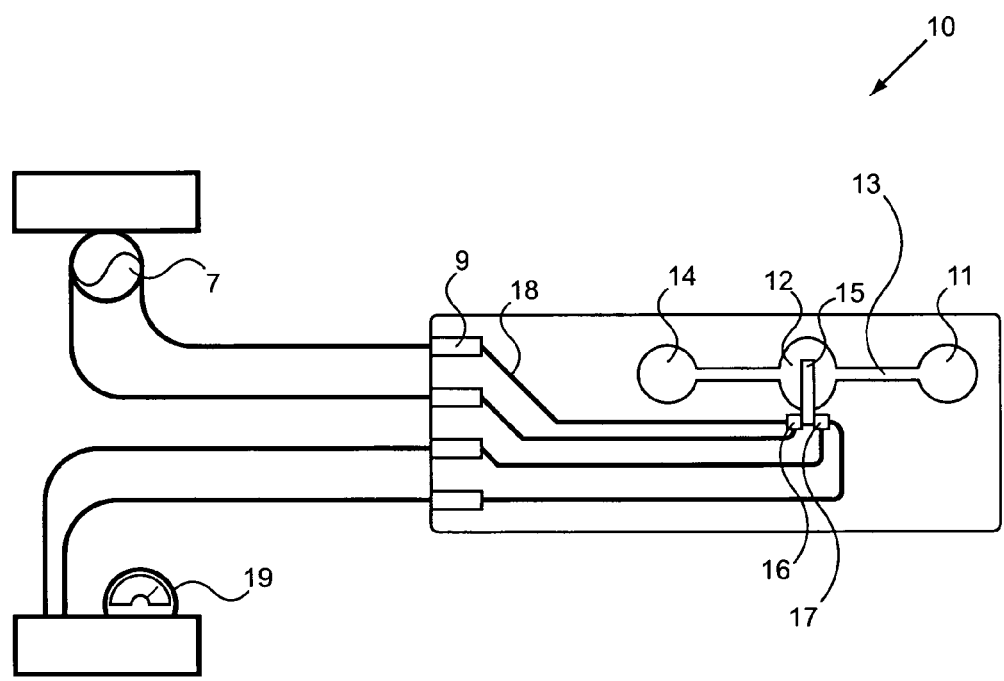
FIG. 2 shows a schematic diagram of a system for detecting the viscosity of a sample by monitoring vibrations of a cantilevered working member in contact with the sample and energized with a piezoelectric actuator.

In a particular embodiment, the device is a cartridge 10 having a sample introduction port 11 in fluid contact with a sample chamber 12 through an inlet conduit 13, as shown in FIG. 2. Excess sample can flow through the sample chamber to a vented waste chamber 14. A working member 15 is cantilever mounted in functional contact with piezoelectric actuator 16 and piezoelectric sensor 17. The actuator 16 is energized by electric current from oscillator 7 through electric leads 18. The sensor 17 is in electrical contact with detector 19 to transmit signals for detection and correlation to physical properties of a sample in the chamber. The actuator 16 function and sensor 17 function can optionally be provided by a single piezoelectric transducer unit. The oscillator and detector are typically not incorporated into the cartridge. In many embodiments, the oscillator 7 and detector 19 are part of a cartridge reader system and the disposable cartridge 10 is inserted into a slot or carriage in the system to establish electrical contact through contacts 9.

Figure 3:
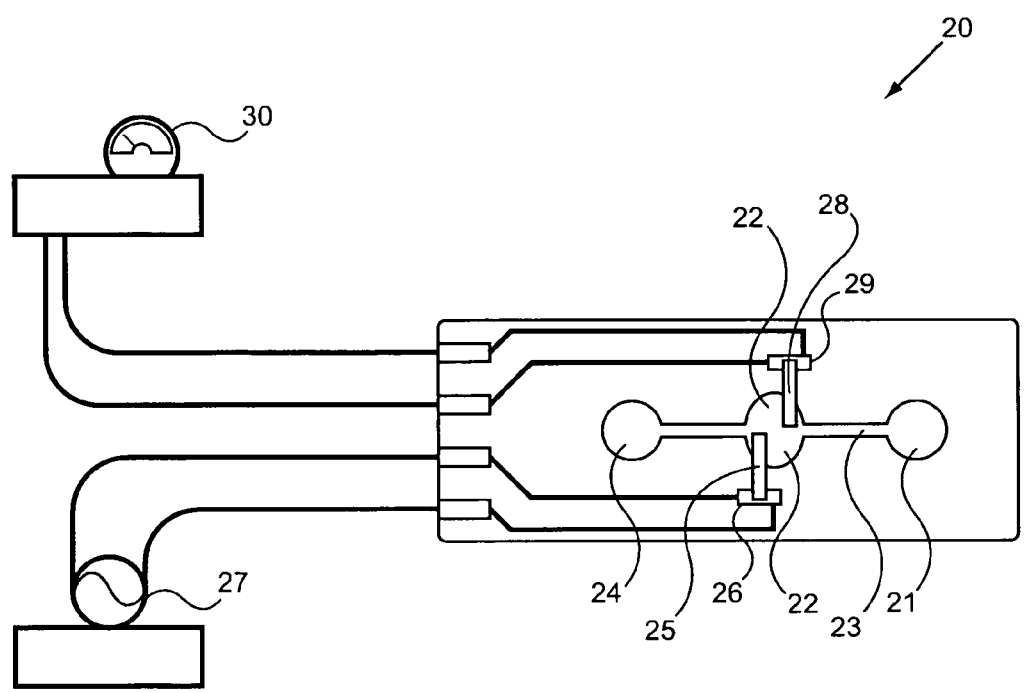
FIG. 3 shows a schematic diagram of a system for detecting the viscosity of a sample by monitoring vibrations transmitted to a sensor member through the sample from a working member energized by a piezoelectric actuator.

In another embodiment, as shown in FIG. 3, the device is a cartridge 20 having a sample introduction port 21 in fluid contact with a sample chamber 22 through an inlet channel

23. Excess sample can flow through the sample chamber to a vented waste chamber 24. A vibrating working member 25 is mounted in functional contact with piezoelectric actuator 26, which is in electrical contact with oscillator 27. A sensing working member 28 having a sample contact surface is in functional contact with piezoelectric sensor 29, which is in electrical contact with detector 30. In operation, a sample is introduced to the sample port and flows to fill the sample chamber. The vibrating member is in contact with the sample to impart vibrations (e.g., physical pressure and/or flow waves), which are received by the sensing member. Depending, e.g., on the viscosity or mass properties of the sample, the amplitude and/or wavelength of the vibrations received at the sensing member can vary in ways correlated to theses properties.

Figure 4A:
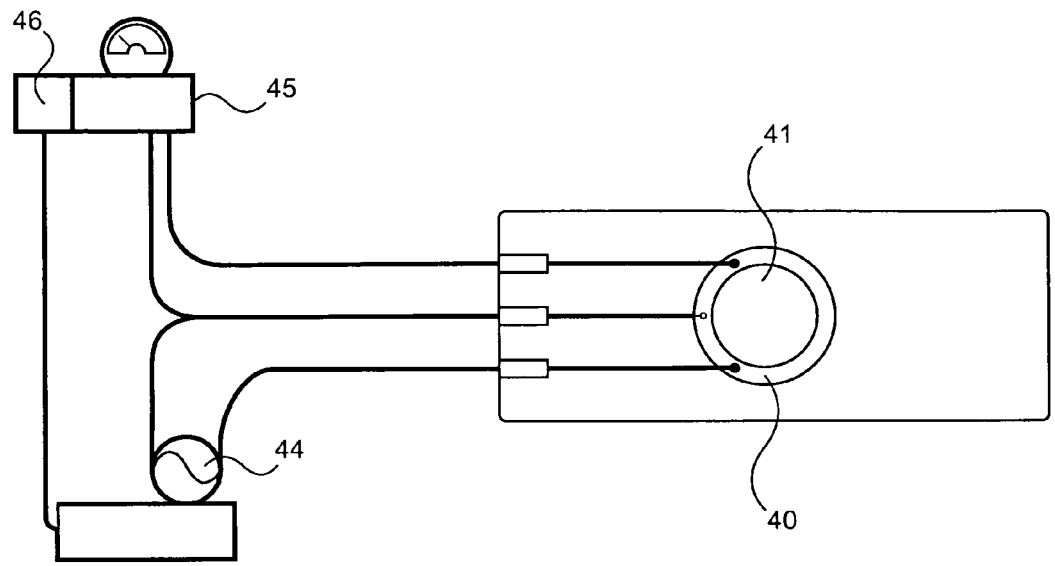
FIGS. 4A and 4B are schematic diagrams of an assay device comprising a dome shaped working member.
Figure 4B:
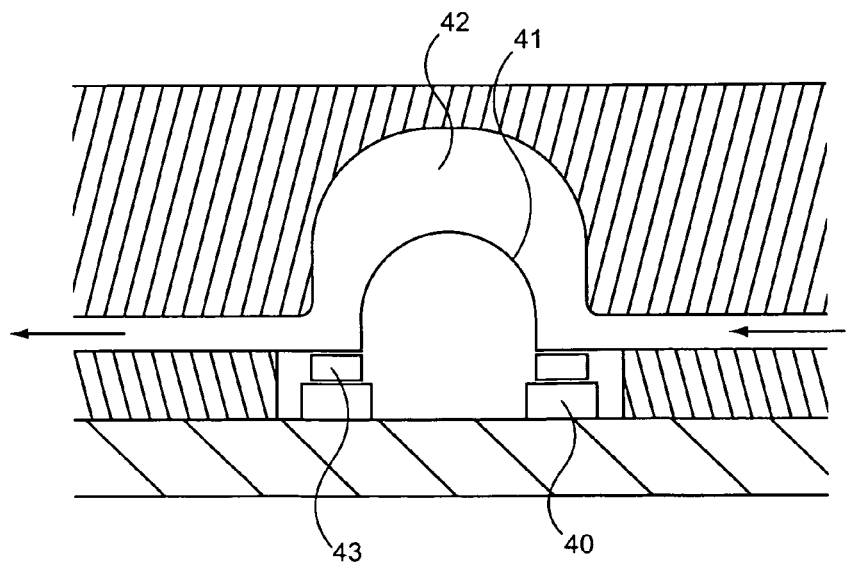

In still another embodiment, as shown in top down view FIG. 4A and cross-sectional view 4B, the working member can be a membrane in contact with the sample of interest. For example, the device can include an annular piezoelectric actuator/sensor 40 associated with, e.g., a dome-shaped working member 41 membrane. A sample chamber 42 is provided, e.g., in contact with one side of the membrane, as shown in vertical cross section FIG. 4B. An annular mounting ring 43 can be provided between the membrane and piezoelectric actuator/sensor 40. An oscillator 44 can be in electrical contact to energize the actuator/sensor, inducing vibrations in the ring, membrane and sample present in the chamber. The surface area and dome shape of the membrane can disperse the outgoing vibrations and provide a physical impedance match between the sample and piezoelectric device. The membrane can also efficiently direct incoming vibrations from the sample back onto the piezoelectric device. A detector 45 can be in electrical contact with the transducer/sensor, e.g., to receive net voltages resulting from interaction of the oscillator induced vibrations and the sample vibrations at the membrane. The amplitude and/or waveform character of the detected signal can be evaluated directly to make inferences about the physical characteristics of the sample. Optionally, a comparator 46 can receive, e.g., waveform information from the oscillator circuit and compare it to the net voltages from the annular piezoelectric device to determine how the sample affected the transmitted vibrations. The differences between the oscillator waveform and sensor signal return can be interpreted to provide an assay result characterizing a physical property of the sample.

Figure 5:
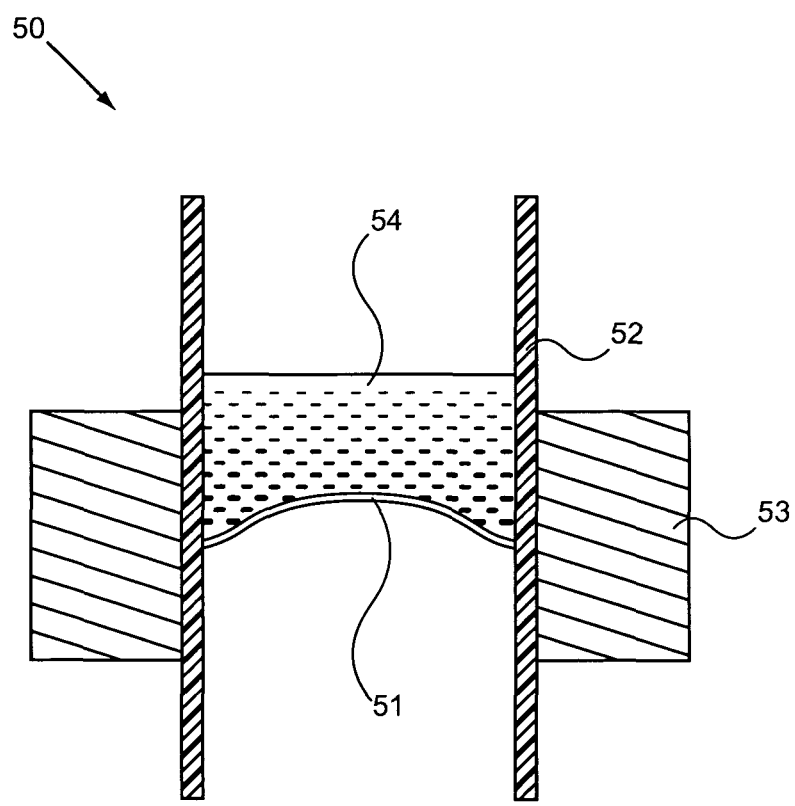
FIG. 5 shows a schematic diagram cross section of a device for detecting sample physical characteristics, wherein the sample chamber is situated inside a tube, the working member is a membrane across the inside of the tube, and the transducer is positioned around the outside of the tube.

In yet another embodiment, the working member is a membrane across a chamber and the transducer is mounted on the outside of the chamber around the periphery of the membrane, e.g., as shown in FIG. 5. For example, a device 50 for detecting a physical property of a fluid can comprise a membrane 51 mounted across the interior of a tube 52 (shown in axial section). Around the periphery of the membrane, on the outside of the tube, a piezoelectric transducer 53 can be positioned to induce and receive vibrations to and from the membrane. In use, a sample 54 can be applied to a surface of the working member membrane 51 so that vibrations transmitted from the transducer 53 (in actuator mode) through the tube 52 wall and to the membrane 51 can enter the sample 54. Vibrations returning from the sample 54 through the membrane 51 and tube 52 wall can be received by the transducer 53 (in sensor mode). In such an embodiment the tube wall can be resilient to transmit vibrations and the membrane can have a dome shape.

Piezoelectric Transducers

Piezoelectric transducers are typically used in the analytical devices of the invention to send vibrations into samples. Transducers are typically fitted with a working member to provide, e.g., leverage and surface area advantages in transmission of the vibrations into the sample. The transducers are typically energized with and AC voltage from an oscillator. In some embodiments of the inventions, a piezoelectric transducer also functions as a receiver or sensor of vibrations returning from the sample (i.e., functions in both actuator and sensor modes).

Piezoelectricity is the ability of some materials to generate an electric field or voltage in response to applied mechanical stress. The effect is said to be result from a relationship between polarization density of the material and the material's volume. A piezoelectric transducer can function as a sensor by providing a detectable voltage in response to a mechanical stress (e.g., vibrations). Conversely, many piezoelectric materials have the ability to change dimensions or provide a mechanical force in response to an applied voltage (e.g., functioning as an actuator). Therefore, a piezoelectric transducer can function as ether an actuator or a sensor, or both, depending on how it is configured to interact with other system components.

There are many natural and man made piezoelectric materials. Sugar crystals and bone can be piezoelectric. Other piezoelectric materials include, e.g., berlinite ($AlPO4$), quartz, gallium orthophosphate ($GaPO4$), 1Langasite ($La3Ga5SiO14$), barium titanate ($BaTiO3$), lead titanate ($PbTiO3$), lead zirconate titanate, potassium niobate ($KNbO3$), lithium niobate ($LiNbO3$), lithium tantalate ($LiTaO3$), sodium tungstate ($Na2WO3$), $Ba2NaNb5O5$, $Pb2KNb5O15$, sodium potassium niobate (NKN), sodium potassium niobate, bismuth ferrite ($BiFeO3$), sodium niobate ($NaNbO3$). Preferred piezoelectric materials in the present inventions include polyvinylidene fluoride (PVDF) and quartz.

Piezoelectric transducers can be of any size and shape appropriate for the proper function of a particular device. Typical transducers in the devices are in the form of an annular ring or slab form.

Piezoelectric transducers can operate in any of several modes. For example, a piezoelectric transducer can be configured as an actuator doing work as an actuator in longitudinal mode, transverse mode, and/or shear mode. The most appropriate mode can depend on, e.g., the orientation of the transducer, the orientation of any associated working member, and the work to be done. To detect the viscosity of a sample, it is often desirable to have vibrations directed across the surface in contact with the sample. If the sample is directly in contact with a surface of the piezoelectric device, or if the device is associated with a working member with contact surfaces parallel to a surface of the device, it can be advantageous to operate the device in shear mode. In other embodiments, e.g., wherein the sample is enclosed in a chamber with a bottlenecked outlet, viscosity of the sample can be efficiently detected by a transducer and/or working member motion that reduces the available volume in the chamber. For example, where the working member is a membrane dome in a sample chamber having narrow outlets and mounted to an annular transducer ring, a transverse motion of the transducer can force the dome into the chamber. The peak forces and back pressure will be higher if the sample is more viscous; the more viscous sample encountering more resistance to flow through the narrow outlet.

In use as a sensor, the piezoelectric transducers can be configured to operate in modes that efficiently receive forces from the sample and convert them into a detectable voltage. For example, where the sensor transducer shares a surface with the sample chamber, pressures in a sample can typically be converted efficiently into a voltage with the transducer in a transverse mode. In configurations wherein the sample is subject to forces that cause it to flow or oscillate across the sensor surface, a shear mode configuration can be desirable for the sensor. When a sensor member is associated with the sensor transducer, the sensor member is preferably mounted to the sensor transducer so that the major movement or force on the member from the sample is co-aligned with the selected mode of operation.

A single transducer can function as both an actuator to vibrate a sample and as a sensor, e.g., to generate voltages in response to vibrations received from the sample. Circuitry and/or logic can be established to interpret or deconvolute the mixture of oscillator voltage inputs and piezoelectric voltages generated by sample pressures. In a simple embodiment, the transducer can be energized with an electric voltage to produce a single pressure wave (or quick series of pressure waves) in the sample, followed by a pause to receive pressure waves that return from the sample. In this way, the working voltages would not have to be subtracted from sample pressure generated voltages in detection and interpretation of a measurement. Alternately, the known input working voltages or other signals from oscillator circuitry can be subtracted from, e.g., the net voltage waveforms, to detect that part of the voltages resulting from pressures returned from the sample. For example, a comparator circuit can receive voltages from the oscillator circuitry and, e.g., subtractively compare them to the net voltages in the piezoelectric transducer to unveil those voltages associated with sample pressures. In another embodiment, a physical and/or electronic resonance frequency is determined to detect a physical property of a sample. Optionally, the resonance frequency can be monitored to detect changes, e.g., of sample viscosity over time.

Working Members

Working members have sample contact surfaces and are mounted to transducers, e.g., to transmit vibrations from the transducer to a sample (actuator mode), and/or to transmit vibrations from a sample to the transducer (sensor mode). Instead of direct contact of the sample to the piezoelectric device, working members can provide a mechanical advantage, e.g., to enhance sensitivity of the device and match impedance between the sample and device.

The working member can have a surface that acts as a surface wall of the sample chamber and/or can protrude into the chamber. In actuator mode, a working member can be mounted directly or indirectly to an actuating device to transmit physical vibrations from the actuator to a sample chamber space. In sensor mode, a working member can be mounted directly or indirectly to a sensing transducer device to receive physical vibrations from the sample chamber space and transmit them to the sensor.

In an actuator mode embodiment, the working member can be configured as a chamber surface wall, e.g., with a membranous working member mounted across an aperture. A piezoelectric actuator can be in broad contact with the back side of the membrane, central contact with the membrane and/or in peripheral contact with the membrane. In preferred embodiments, at least part of the membrane back (non sample contact) side is not in direct or indirect contact with the piezoelectric actuator (e.g., but in contact with a gas phase). In many such embodiments, it is advantageous to have the actuator in transverse mode, e.g., with motion transmitted in a vector perpendicular to the plane of the membrane, thereby directing vibrational waveforms into the sample space. Optionally, dome-shaped working members can be mounted about the peripheral edge to a circular, planar or annular ring piezoelectric actuator. The actuator can function in shear mode, e.g., vibrating the dome edges axially (perpendicular to the central axis) to impart waves to the center of the dome. Alternately, the actuator can function primarily in the transverse mode, e.g., vibrating the dome edges coaxially.

In a sensor mode embodiment, the working member can be configured as a chamber surface wall, e.g., with a membranous working member mounted across an aperture. A piezoelectric sensor can be in broad contact with the back side of the membrane, central contact with the membrane and/or in peripheral contact with the membrane. The piezoelectric actuator can be configured in transverse mode, e.g., to receive motion transmitted from the membranous working member in a vector perpendicular to the plane of the membrane, thereby receiving waveforms impacting the membrane from the sample space. Optionally, dome-shaped working members can be mounted about the peripheral edge to an annular ring piezoelectric sensor. The sensor can function in shear mode, e.g., receiving lateral vibrations from axial movements out from dome edges. Alternately, the sensor can function primarily in the transverse mode, e.g., to efficiently receive vibrations traveling coaxially from dome walls.

In actuator mode, the working member can be configured as, e.g., a cantilevered beam extending into the chamber volume. For example, the working member can extend perpendicular to the chamber wall into the chamber volume. The afferent end of the member can be functionally mounted to a piezoelectric actuator. The base of the member can be resiliently or fixedly mounted to the chamber wall where it passes through. Optionally, the member can be mounted to the actuator and the actuator can provide at least a part of the chamber interior surface. In preferred embodiments, the piezoelectric actuator is not in direct contact with the chamber interior. The cantilevered working member can interact with the actuator to provide vibration motions largely along the length of the member, e.g., in a sliding shear motion with a sample in the chamber. In a preferred embodiment, the cantilevered working member can interact with the actuator to provide vibration motions largely across the length of the member, e.g., in motions pushing sample laterally.

In certain sensor mode embodiments, the working member is configured, e.g., as a cantilevered beam protruding into the chamber volume. Physical oscillations (e.g., vibrations) in a sample can be transmitted from a sample in the sample chamber, through the sensor working member rod, to a piezoelectric sensor. The sensor can be configured to receive vibrations primarily from along the axis of the rod. In preferred embodiments, the sensor is configured to receive vibrations propagated primarily across the axis of the rod.

In some embodiments, the actuator is a membrane and the sensor is a cantilever. In a more preferred embodiment, the actuator is a cantilevered beam and the sensor is a membrane.

Working members can have dimensions suitable to effectively interact with other device components. For example the shape and dimensions of working members can depend on the size of the chamber, contact surface area with the piezoelectric device, force and stroke of the piezoelectric device, and density of the sample. The membranous working members can have a sample contact surface area of, e.g., from more than 10 cm$^2$ to less than 0.001 mm$^2$, from 1 cm$^2$ to 0.01 mm$^2$, from 0.1 cm$^2$ to 0.1 mm$^2$, from 0.01 cm$^2$ to 0.1 mm$^2$, or about 1 mm$^2$. The membranous working members can have a thickness ranging from more than about 1 mm to less than about 1 nm, from 0.1 mm to 10 nm, from 0.01 mm to 100 nm, or about 1 μm. The membranous working members can have at least one dimension ranging from more than 1 cm to less than about 1 μm, from 1 mm to about 10 μm, or about 100 μm. A typical cantilevered beam working member can have a thickness ranging from more than about 1 mm to less than about 1 nm, from 0.1 mm to 10 nm, from 0.01 mm to 100 nm, or about 1

μm to 5 μm. The cantilevered working members can have a length ranging from more than 1 cm to less than about 1 μm, from 1 mm to about 10 μm, or about 100 μm. The cantilevered beam will typically have a length to thickness or length to width ratio of ratio of more than 2, more than 5 or more than 10.

Working members can be of any appropriate material. For example, working members can be fabricated from MEMS materials, plastics, metals, metal alloys, ceramics, glass, fluorocarbon polymers, and/or the like.

Sample Chambers

Sample chambers receive samples for analysis. Sample chambers of the invention provide a surface and/or internal space for transducers and/or working members to physically interact with samples.

Samples can be introduced into sample chambers directly, e.g., by a technician introducing the sample directly through a sample port, using a pipettor. Optionally, samples can flow through a conduit, e.g., from a loading chamber, into the sample chamber, with excess sample flowing on to a vented waste chamber. The chamber and channels can have capillary scale dimensions and/or hydrophilic surfaces, conducive to capillary flow. Optionally, sample fluid can flow under the force of a pneumatic or hydraulic pressure, gravity, electroosmosis, centripetal force, and/or the like.

In many embodiments, the devices of the invention include two or more sample chambers. For example, a cartridge can include channels in fluid contact with one or more sample test chambers, one or more control sample chambers and/or one or more standard reference sample chambers. In this way, replicate test samples can be tested, for more accurate or precise final results. Control samples can be tested to confirm the assay is functioning within predetermined variation limits. Standard samples can be tested to provide reference for correction of test sample results or to provide regression data for preparation of a standard curve.

Sample chambers can be configured to enhance sensitivity of an assay. For example, where there are separate actuator and sensor working members, the sample chamber can be configured to efficiently transmit energy into the sample and to efficiently focus transmitted waveforms from the sample onto the sensor member. In one embodiment, the chamber walls expand smoothly in cross section away from the actuator and converge smoothly toward the sensor actuator, e.g., to focus the transmitted energy on the sensor member.

Sample chambers can have any shape appropriate to function of a particular actuator/sensor system. In embodiments with a single cantilever actuator/sensor, it can be preferred that the sample chamber be shaped, e.g., as a cone, half dome or ¾ dome, with the cantilever at the center bottom to efficiently transmit, reflect and focus sample vibrations on the member. In embodiments where there are separate actuator and sensor members in the chamber, it can be preferred to have them located at or near opposite ends of a chamber expanding out from the actuator and converging back on the sensor. In some embodiments, the chamber can be in the shape of a conic section with the sensor and/or actuator at a focal point. In embodiments where the member is a dome-shaped membrane, it can be preferred that the sample chamber have an expanded complimentary dome shape to reflect vibrations back for sensing. Because many samples for testing are non-compressible, it is preferred the sample chamber be vented, include an air space, or include an exit channel to allow sample vibration movements. In many cases, it is preferable to position the sensor near the vent or exit, or between the actuator and the vent or exit, e.g., to optimally expose the sensor to the vibration forces. Optionally, the sample chamber can be resilient to change shape or volume to accommodate sample vibrations. In one embodiment, the sample chamber is a resilient tube transected across the axis by a working member membrane and surrounded by a transducer; the chamber space defined by the tube wall and membrane.

Sample chambers can have dimensions and volumes suitable to a particular system and sample. For example, the sample chambers can have a tested sample volume ranging from more than 10 $cm^3$ to less than 0.01 μl, 1 $cm^3$ to 0.1 μl, 100 μl to 1 μl, or about 10 μl. The sample chambers can have at least one dimension ranging from more than 10 cm to less than about 1 μm, from 10 mm to about 10 μm, or about 1 mm.

In many embodiments of the devices, the sample chamber is defined as a void in a laminated layered structure. For example, a first layer of material can have a cut out section in the desired shape of the sample chamber. The first layer can include cut outs (e.g., defining side walls) for additional spaces, such as, e.g., channels, reaction chambers, waste chambers, and the like. The first layer can be laminated between a top cover layer and a bottom substrate layer, thereby functionally sealing the voids designed into the first layer. In preferred embodiments, the sample chamber fills an area between an actuator and a sensor. The top and bottom layers can comprise the transducers and working members adjacent to the sample chamber space. Alternately, transducers and/or members can be built into the same layer as the sample chamber void, e.g., at opposite ends of the chamber cut out.

Optionally, the sample chambers can be, e.g., tubular conduit with the transducer and members mounted to or through the conduit walls. In a preferred embodiment, the sample chamber has an increased cross section in a space between the actuator and sensor.

Samples

Devices of the invention measure physical parameters of samples of interest. The samples are typically fluids, liquids, gels, semisolids, and/or the like. In many embodiments of the devices, physical parameters (characteristics) of interest in the samples include, e.g., sample density, viscosity, mass, tenacity, resilience, and/or the like. In typical embodiments, the viscosity of the sample is of key interest.

Samples for analysis in the methods of the invention are typically fluids. For example, samples of interest can be body fluids such as whole blood, blood plasma, clotted blood, cerebrospinal fluid (CSF), synovial fluid, amniotic fluid, and/or the like. Measurable physical characteristics of fluids in industrial processes can also be of interest. For example, the present devices can be used to measure the melting or polymerization process materials such as, e.g., glass, sugar, food recipes, plastics resins, and/or the like. In certain instances, the samples are dynamic, with changing physical characteristics that can be detected or followed with time. For example, the devices of the invention can follow the progress of clot formation in blood, the polymerization of a plastic, or changes in a stream of process materials as they pass through the sample chambers of the invention.

Methods of Detecting Sample Physical Characteristics

Methods of sample analysis include, e.g., preparation of the sample, introduction of the sample to a sample chamber, vibrating the sample with an actuator through a working member, receiving vibrations transmitted through the sample and a working member to a sensor, detecting a signal output from the sensor, and correlating the signal to a physical characteristic of the sample. The methods of sample analysis are typically carried out using devices for detecting physical characteristics of a fluid sample, as described above.

Preparing Samples

In many cases, samples of interest can be effectively analyzed according to methods of the invention, without significant preparation. In many other cases, the samples should be adjusted, e.g., to lower background noise, initiate changes in physical properties for evaluation and/or to improve the flowability of the sample before introduction into a sample chamber.

It can be desirable to remove particles and other materials that affect the uniformity of a sample of interest. For example, a sample can be centrifuged or filtered to remove particles or polymerized sample constituents that could clog device channels or interfere with transmission of vibrations through the sample. In many embodiments, samples can be treated to remove unwanted constituents by filtering them through, e.g., a filter provided in a sample inlet port, or in a channel or chamber leading to the sample chamber.

Samples can be adjusted for analysis, e.g., by initiating, completing or stopping reactions that can influence the physical characteristic of interest to be measured. For example, whole blood can be anti-coagulated to retain a liquid suspension form during handling and processing. The anticoagulant can be neutralized and a clot promoting reagent can be introduced before initiation of analysis. For example a tissue factor and calcium salts can be added to the a plasma sample before introduction of the sample into the device, in a sample port, in a sample channel or in the sample chamber, to initiate a clotting reaction to be analyzed. Optionally, a polymerization catalyst can be added to monomers before analysis of a polymerization reaction.

In many embodiments, the sample is introduced into the sample chamber, where the same sample aliquot resides without leaving the chamber during the analysis. In other embodiments, the sample can comprise a stream of sample flowing through the sample chamber, e.g., with two or more assay data points being collected over time. For example, a stream of sample can be monitored to detect when the sample has reached a desired density of degree of polymerization.

Detecting a Physical Characteristic of a Sample

With a prepared sample in the sample chamber, a physical characteristic of the sample can be detected, e.g., by vibrating a working member in contact with the sample and detecting the characteristics of vibrations transmitted through the sample.

In one embodiment, the viscosity or resilience of a sample can be detected by contacting a cantilevered working member with the sample, vibrating the working member with a piezoelectric transducer working at a frequency established by an oscillator circuit; and detecting the frequency or amplitude of vibrations actually induced into the sample. For example, the piezoelectric transducer and working member can function as both an actuator/member pair and as a member/sensor pair. A detector can monitor the oscillator input voltages and compare them to voltages actually present in the piezoelectric transducer, which voltages are modulated by vibrations received back from the sample (or the samples influence on the ultimate harmonic frequency of the system as a whole). Typically, a more viscous or dense sample will dampen the working member vibrations result in, e.g., a lower resonant frequency and/or lower amplitude in the sample or member than in the oscillator (e.g., unloaded) input. In another embodiment, the single actuator/sensor can include a membrane (e.g., dome) member transmitting vibrations from and to one or two or more piezoelectric transducers in functional contact with the member.

In embodiments of the invention, the oscillator, transducer, working member and/or sample can be energized to oscillate or physically vibrate at a frequency of choice. The choice of frequency can be determined empirically or by calculation. The frequency of choice can depend on, e.g., the mass and action arm of individual interacting components of a particular device. For example, a frequency can depend on the mass, size and shape of the sample, transducer and membrane. In many embodiments, it can be desirable to choose a frequency that provides a good impedance match between the physical and electronic components of the device, e.g., to provide an efficient resonance between the components. This is often easy to provide by simply tuning the amplitude and/or frequency of the oscillating power source for the system. Preferred frequencies for vibrations in the systems can range, e.g., from less than about 100 Hz to more than about 1 MHz, from about 1 kHz to about 500 kHz, from about 250 kHz to about 10 kHz, or about 25 kHz. Physical properties of a sample in such a system can be determined by detecting the effect the sample has on the resonant frequency of the system. Typically, a more massive, dense or viscous sample will tend to slow the resonant frequency of the system.

In another embodiments, the actuator and sensor can include separate transducers and working members. For example, the viscosity of a sample can be detected by contacting a cantilevered working member with the sample, vibrating the working member with a piezoelectric actuator working at a frequency established by an oscillator circuit; transmitting vibrations through the sample to a sensor working member, sensing vibrations in the sensor member with a piezoelectric sensor and detecting the frequency, phase or amplitude of the sensor vibrations. The actuator member and sensor member can be, e.g., cantilever rods running parallel to each other at opposite ends of the sample chamber. Alternately, the actuator member can be a cantilevered beam and the sensor member can be a membrane at the other end of the sample chamber.

Correlating Sensor Signals With Sample Characteristics

Signals from sensors can be correlated to a physical characteristic of the sample. Single time point measurements of sensor voltage, current, resistance or waveform can be correlated to, e.g., an viscosity, density, mass, temperature, and/or extent of polymerization a sample at that point in time. Optionally, a time point of interest in a changing sample can be determined based on a signal reaching a certain magnitude, or rate of change end point.

To determine the condition of a sample at a given time, a detected signal can be correlated to a standard curve. For example, a regression curve can be developed presenting a range of voltage amplitudes (or viscosities) for standard samples versus their associated coagulation state. The coagulation state of an unknown test sample can then be determined from the chart by reading the state correlated to a voltage amplitude determined for the test sample.

In an embodiment of the invention, activated partial thromboplastin times for a variety of different standard samples can be determined according to standard methods. The standard samples can then be analyzed using a device of the invention to determine, e.g., a viscosity, for each sample, e.g., which correlates with the known aPTT times for the samples. From this data, a standard regression curve can be constructed correlating known aPTT times to viscosity values (or measured voltage amplitudes in the sensor), for the samples. Given the standard regression curve, the aPTT time for an unknown sample can be determined based on a viscosity (or amplitude signal), determined according to the methods of the invention.

It is often desirable to improve the confidence, precision and accuracy of a determination by including replicate test samples, controls and/or standard references in an assay. For example, multiple sample aliquots can be tested in parallel in multiple sample chambers on the same assay cartridge. An assay cartridge can include control samples to confirm a particular assay has read out results within a predetermined acceptable range. An assay cartridge can include sample chambers for analysis of standard reference samples, e.g., to provide standard results for calculation of unknown sample results.

EXAMPLES

The following examples are offered to illustrate, but not to limit the claimed invention.

The prothrombin time (PT) measures the function of the coagulation extrinsic pathway. In a clinical setting, the PT is used to determine the clotting tendency of blood, monitor warfarin dosage, to detect liver disease, and can suggest a vitamin K deficiency. The normal range for prothrombin time is usually around 12-15 seconds In a standard PT assay time, blood is drawn into a test tube containing liquid citrate, which acts as an anticoagulant by binding the calcium in a sample. The blood is mixed, then centrifuged to separate blood cells from plasma. An excess of calcium is added (thereby reversing the effects of citrate), along with tissue factor (also known as factor III or thromboplastin). The time the sample takes to clot at 37° C. is traditionally detected mechanically or optically.

A PT can be determined using the methods and devices of the present invention. For example, in view of FIG. 2, citrate anti-coagulated blood plasma is introduced into sample introduction port 11, which has a porous matrix filter effectively trapping particles larger than about 50 µm. The plasma flows through channels by capillary action to fill the sample chambers 12, which contains coagulation reagents. Excess plasma flows into vented waste chambers 14. In the inlet conduit 13, the plasma comes into contact, and mixes with the reagents comprising calcium salts and thromboplastin, thus initiating coagulation of the test sample.

An oscillator 7 in electrical contact with piezoelectric transducer 16 provides an AC current of 20 kHz. The oscillating electric current in the transducer produces vibrations, transmitted through working member 15 into the blood plasma sample in the sample chamber.

The mass and viscosity of the sample influence the vibration amplitude and frequency of the working member. Further, pressure waves returning to the working member from the sample interact with the working member vibrations to create harmonic and beat frequencies. The net result is that the voltages and wave forms in the piezoelectric transducer are different in many ways as compared to voltages and waveforms in the oscillator circuit. These voltages and waveforms are detected by detector 19 in electrical contact with the sensor electrodes.

A logic circuit, e.g., with a comparator function, in the detector can compare, e.g., the voltages or waveforms present in the sensor and oscillator circuits. At early time points, the plasma sample is uncoagulated, however as coagulation progresses in the sample chamber, viscosity of the sample increases, resulting in progressively lower amplitudes and longer wavelengths detectable in the sensor circuit.

A computer receives and stores the sensor output data values over a series of time points. The amplitude of vibrations received in the sensor circuit varies in a sigmoid fashion with time. For example, when the sample is uncoagulated, the working member vibrates at a high amplitude at a frequency close to oscillator unloaded frequency. However, as the sample continues to coagulate, the viscosity rises and inhibits motion of the working member, and the amplitude of the vibrations slows rapidly. At a certain point, the rate of change (charted slope) in the vibration frequency or amplitude reaches a maximum. Finally, the sample nears maximum coagulation and viscosity and the frequency or voltage amplitude levels off to approach a base level.

Any point in the sigmoid curve can be selected as an end point in the assay and correlated to standard PT assays, e.g., on the same samples. However, the most precise and repeatable end points for use in the assay are typically the inflection point of maximum slope (highest rate of change) and the time point where the difference is half way between the starting values and base level value. These end points are readily determined by commonly available data analysis software.

The selected end time points can be reported out directly as clotting times determined by the device. Optionally, the time points can be correlated to standard PT times, e.g., using a regression curve, and reported out as standard PT results.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations and permutations, all of which cannot reasonably be recited individually in this document, but can be understood by one of skill in the art on review of this specification.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A device for measuring physical characteristics of a sample, the device comprising:
   an annular piezoelectric transducer comprising a central opening;
   a working member membrane comprising a sample contact surface and mounted across a central axis of the transducer over the central opening; and,
   a detector circuit in electrical contact with the transducer;
   wherein the sample chamber comprises a tube running through the central opening of the annular transducer and the membrane is mounted across an interior of the tube;
   whereby vibrations in the working member membrane are transmitted to the transducer inducing electrical resistance, voltage, current or waveform changes in the transducer which are detectable by the detector.

2. The device of claim 1, wherein the central opening comprises a circular circumference.

3. The device of claim 1, wherein the central opening has a diameter ranging from 10 mm to about 0.1 mm.

4. The device of claim 1, wherein the membrane is dome shaped projecting away from the central opening.

5. The device of claim 1, wherein the membrane comprises a thickness ranging from about 0.2 mm to about 0.0005 mm.

6. The device of claim 1, further comprising an electrical oscillator in electrical contact with the transducer, whereby electrical oscillations from the oscillator induce vibrations in the transducer.

7. The device of claim 1, wherein the transducer is configured in shear-mode across a major plane of the transducer.

8. The device of claim 1, further comprising the sample, which sample comprises a fluid or gelatinous material in contact with the sample contact surface.

9. The device of claim 1, further comprising an annular mounting ring comprising an aperture, wherein the membrane is mounted across the aperture and the ring is between the membrane and the annular transducer.

10. The device of claim 1, wherein the detector is adapted to detect a change in viscosity, mass or density of a fluid in contact with the sample contact surface according to a correlation with the electrical change.

11. The device of claim 1, further comprising a sample chamber defining an inner space, wherein the sample contact surface of the working member is in contact with the space.

12. The device of claim 11, further comprising a reagent in fluid contact with the inner space or within the inner space.

13. The device of claim 1, adapted to measure the physical characteristic of viscosity.

14. A device comprising:
a piezoelectric transducer;
an oscillator in electrical contact with the transducer;
a working member in functional contact with the transducer and comprising a sample contact surface in fluid contact with a sample chamber; and,
a detector in electrical contact with the transducer;
wherein the sample chamber comprises a tube running through the transducer and the working member is mounted across an interior of the tube;
whereby vibrations can be imparted to the working member from the transducer and electronic parameters can be detected in the transducer by the detector;
wherein the parameters are selected from the group consisting of electrical resistance, voltage, current, resonant frequency, and waveform.

15. The device of claim 14, wherein the transducer is annular with a central aperture and the working member is a dome shaped membrane mounted across the aperture.

16. The device of claim 14, wherein the working member is in functional contact with the transducer at a mounting surface; and, wherein most of the sample contact surface is not in a plane parallel to the mounting surface.

17. The device of claim 14, wherein the working member is a cantilevered beam in contact with the transducer at one end but not at the opposite end.

18. The device of claim 14, further comprising a sample in contact with the sample contact surface.

19. The device of claim 18, wherein most of the sample contact surface is not between the sample and the transducer.

20. The device of claim 14, wherein the device is a microelectromechanical (MEMS) device.

21. The device of claim 14, wherein the detector is configured to detect a change in viscosity, mass or density of a fluid in contact with the sample contact surface according to a correlation with the electrical parameter.

22. A device for detecting a physical characteristic of a sample, which device comprises:
a sample chamber defining an inner space;
a piezoelectric actuator in functional contact with a working surface in contact with the inner space; and,
a piezoelectric sensor in functional contact with at sensor surface in contact with the inner space;
wherein the sample chamber comprises a tube running through the actuator or the sensor, and the working surface or sensor surface is mounted across an interior of the tube; and
wherein the device is configured to transmit vibrations from the actuator working surface, through the chamber space, and to the sensor surface for detection.

23. The device of claim 22, wherein the inner space has at least one dimension less than 0.2 mm.

24. The device of claim 22, wherein the actuator is in functional contact with the working surface through a working member.

25. The device of claim 22, wherein the actuator and sensor are not laminated together.

26. The device of claim 22, further comprising a liquid or gelatinous sample in the inner space.

27. The device of claim 22, further comprising one or more additional sample chambers for detection of replicate test samples, control samples or standard reference samples.

28. A method of detecting a physical characteristic of a sample, the method comprising:
providing a piezoelectric transducer comprising a central opening;
providing a sample chamber comprising a tube running through the central opening of the transducer;
providing a working member membrane comprising a sample contact surface and mounted across the central opening of the transducer;
contacting the sample contact surface with a sample;
vibrating the working member membrane with the transducer;
detecting a voltage, resistance, current, resonant frequency or waveform in the transducer; and,
correlating the detected voltage, resistance, current, resonant frequency or waveform with the physical characteristic of the sample.

29. The method of claim 28, wherein the transducer is provided with a shear-mode in a major plane of the transducer.

30. The method of claim 28, wherein the sample is a biological fluid or polymerizing resin.

31. The method of claim 28, wherein said detecting comprises measuring the voltage, resistance, current or waveform at two or more time points, thereby detecting a change in the viscosity of the sample.

32. The method of claim 28, wherein the sample chamber is in fluid contact with the sample contact surface and retains the sample; and,
further comprising providing a reagent in the chamber that reacts with the sample to provide a change in sample viscosity.

33. The method of claim 28, wherein the physical characteristic of the sample is selected from the group consisting of: a viscosity, a density, and a mass.

34. A method of detecting a physical characteristic of a sample, the method comprising:
providing a piezoelectric transducer in functional contact with a working member having a sample contact surface;
providing a sample chamber comprising a tube running through an opening in the transducer;
mounting the working member across an interior of the tube;

providing a sample in contact with the contact surface;

inducing a vibration from the piezoelectric transducer, through the working member contact surface into the sample;

providing a detector in electrical contact with the transducer;

detecting an electrical parameter of the transducer with the detector; and, correlating the parameter with the physical characteristic of the sample in contact with the sample contact surface.

35. The method of claim 34, wherein the sample is a biological fluid or polymer resin.

36. The method of claim 34, wherein the vibration ranges from about 1 kHz to about 500 kHz.

37. The method of claim 34, wherein said detecting comprises measuring the parameter at two or more time points, thereby detecting a change in the physical characteristic of the sample.

38. The method of claim 37, wherein the sample is whole blood or plasma and a clotting time is determined by said detecting the viscosity change.

39. The method of claim 34, wherein the sample chamber is in fluid contact with the sample contact surface and retains the sample; and, further comprising providing a reagent in the chamber that reacts with the sample to provide a change in the sample characteristic.

40. The method of claim 34, wherein the sample contact surface is not a surface of the piezoelectric transducer or a surface immediately adjacent to the piezoelectric transducer.

41. The method of claim 34, wherein the physical characteristic of the sample is selected from the group consisting of: a viscosity, a density, and a mass.

42. A method of detecting a physical characteristic of a sample, the method comprising:

providing a sample chamber defining an inner space;

providing a piezoelectric actuator in functional contact with a working member comprising a working surface in contact with the inner space;

providing a piezoelectric sensor in functional contact with a sensor surface in contact with the inner space;

wherein the sample chamber comprises a tube running through the transducer or through the sensor, and the working member is mounted across an interior of the tube;

providing a sample in the chamber inner space;

vibrating the piezoelectric actuator, thereby transmitting vibrations from the working surface through the sample to the sensor surface;

detecting the vibrations transmitted to the sensor; and correlating the detected vibrations to the physical characteristic of the sample.

43. The method of claim 42, wherein the inner space comprises at least one microscale dimension.

44. The method of claim 42, wherein the sample comprises a biological fluid or polymer resin.

45. The method of claim 42, wherein the vibration ranges from about 1 kHz to about 500 kHz.

46. The method of claim 42, wherein said detecting comprises measuring the voltage, resistance or current at two or more time points, thereby detecting a change in the characteristic of the sample.

47. The method of claim 42, further comprising providing a reagent in the inner space that reacts with the sample to provide a change in sample characteristic.

48. The method of claim 42, wherein the physical characteristic of the sample is selected from the group consisting of: a viscosity, a density, and a mass.

* * * * *